Figure 1:
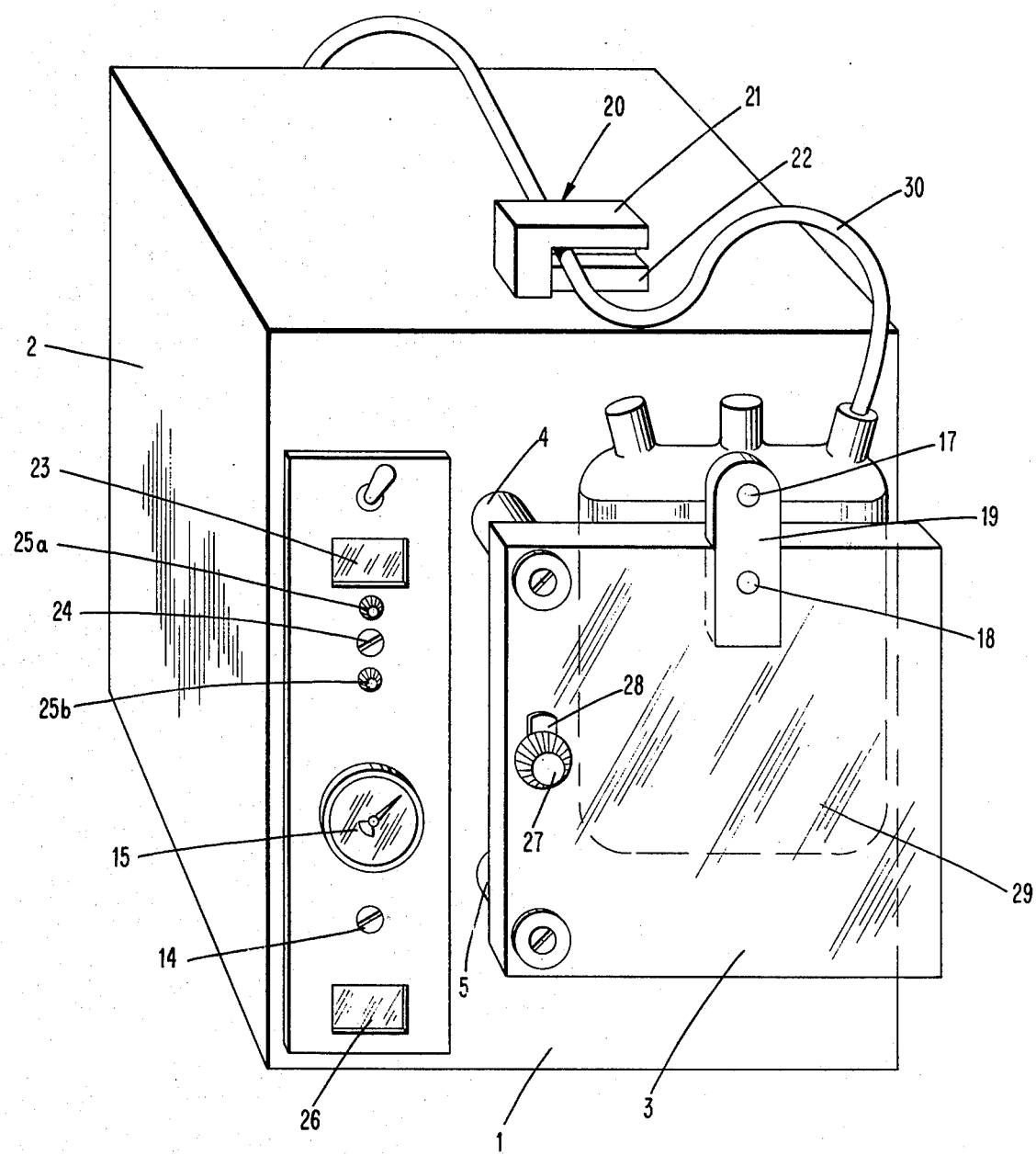

United States Patent [19]
Johansson et al.

[11] 4,350,585
[45] Sep. 21, 1982

[54] DEVICE FOR BLOOD SEPARATION

[76] Inventors: Anne S. Johansson, Vråkvägen 7A, S-752 52 Uppsala; Claes F. Högman, Statarvägen 14, S-752 45 Uppsala; Kenneth G. Hedlund, Skiftesvägen 1, S-754 60 Uppsala, all of Sweden

[21] Appl. No.: 133,867

[22] Filed: Mar. 25, 1980

[30] Foreign Application Priority Data

Mar. 28, 1979 [SE] Sweden .............................. 7902760

[51] Int. Cl.³ .......................................... B01D 21/26
[52] U.S. Cl. .................................... 210/94; 210/96.1; 210/97; 210/523; 210/927; 128/272
[58] Field of Search ............... 210/744, 745, 782, 927, 210/86, 94, 96.1, 97, 523; 128/272

[56] References Cited
U.S. PATENT DOCUMENTS 3,328,255  6/1967  Ilg ..................... 210/927 X
3,551,330  12/1970  Dernquist ..................... 210/745

Primary Examiner—John Adee
Attorney, Agent, or Firm—Burns, Doane, Swecker & Mathis

[57] ABSTRACT

The invention relates to a device for blood separation by squeezing out blood components from a blood bag (29) having at least one outlet conduit (30), said device comprising a support surface (1) and a pressure surface (3) being movable relatively to the support surface and arranged for compressing a blood bag (29) inserted between the pressure surface (3) and the support surface (1). The pressure surface (3) is arranged essentially in parallel with the support surface (1) and drive means are provided for displacement of the pressure surface (3) substantially perpendicularly to the support surface (1) for compressing the blood bag (29) essentially uniformly over the entire surface thereof, and it is provided with at least one sensing device (17, 18), which is arranged to detect when a pre-selected blood component layer has reached a given level in the blood bag (29) and in response thereto to activate means (20) for shutting-off at least one of said outlet conduits (30).

13 Claims, 2 Drawing Figures

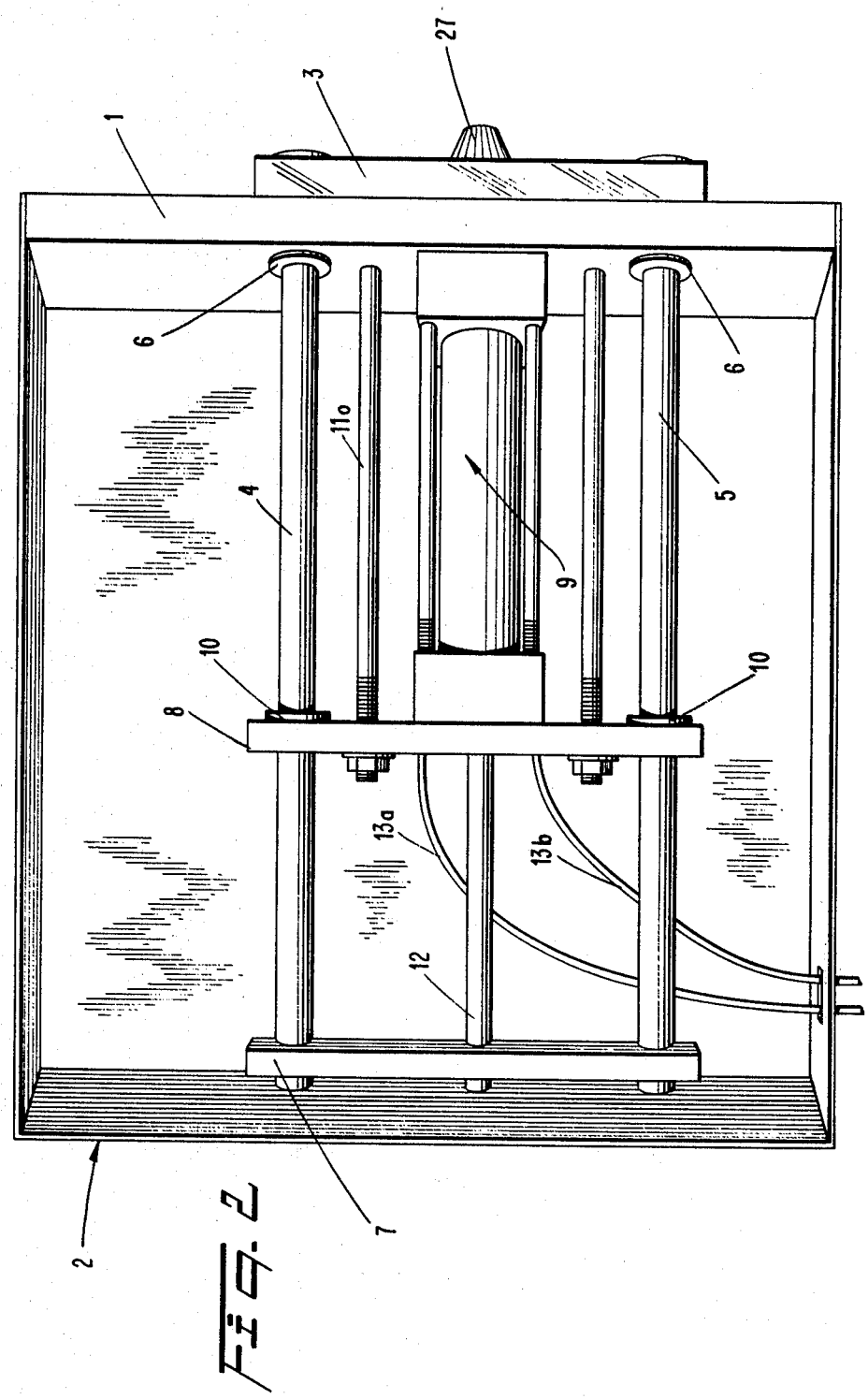

DEVICE FOR BLOOD SEPARATION

The present invention relates to an improved device for squeezing out blood components from a blood bag in connection with blood separation.

When collecting, storing and administering whole blood it is often necessary to separate the cell components of the whole blood from the plasma part so that the plasma part of the blood can be administered to certain patients, the thrombocyte part of the whole blood can be administered to certain patients, and the remaining erythrocytes can be administered to certain patients. In a frequently used technique for providing such separation whole blood from a donor is collected in a blood bag, which is then centrifugated to form an upper blood plasma layer, a thin intermediate so-called buffy coat layer containing leucocytes and possibly thrombocytes, and a lower layer of erythrocytes. By compression of the collection bag the blood plasma is then forced into another blood bag which is sterile connected to an opening in the top portion of the collection bag via a connecting tube. In the same manner the buffy coat layer can be pressed into another blood bag, which may be connected to the same outlet tube, for leaving essentially only erythrocytes in the collection bag. Various devices for the squeezing process as such are known. A typical such device consists of a stationary vertical plate and a movable plate, which is hingedly attached to the lower portion of the stationary plate such that the two plates form a V. The movable plate is spring biased so that the two plates contact each other when the spring is in the resting position. For squeezing out the contents of a blood bag the movable plate is turned out from the stationary plate for loading the spring, whereupon the blood bag is placed between the two plates. Due to the spring force a positive pressure is created in the blood bag thereby squeezing out the contents of the bag. Although this device is simple and reliable it has several drawbacks. It is thus necessary to continuously monitor the squeezing operation so that the same can be stopped when the next layer has reached the top edge of the bag. Furthermore, the blood bag will not be compressed uniformly, but the lower portion will be compressed more rapidly than the upper portion. This is a drawback when squeezing out the buffy coat layer. For squeezing out the same one normally has to assist manually since the leucocytes have a tendency to stick to the walls of the bag. The squeezing would therefore by promoted by a smaller area of the layer at the upper portion of the bag. A further drawback is that the spring force decreases during the compression of the blood bag, whereas in contrast thereto a higher pressure would have been required for pressing out e.g. the more viscous buffy coat layer. The described device cannot either be used for squeezing out the contents of the bag in an upside down position, or in blood bags having an outlet opening in its bottom portion.

The invention inter alia aims at providing a device which eliminates the above indicated drawbacks. This is obtained by means of a device having the characteristics indicated in the subsequent claims.

A basic concept of the invention is thus to provide for essentially uniform compression of the blood bag over the entire bag surface. This is achieved by means of a pressure plate which is essentially parallel displaced towards a stationary plate or wall instead of pivoting towards the stationary plate as in the known device.

According to another basic concept of the invention the device has an automatic shut-off function for the plasma flow. This can be achieved in simple manner by means of one or more suitable positioned sensing means, such as photocells, and shut-off means for a tube outlet from the blood bag controlled by the sensing means. The sensing means are then arranged to activate the shut-off function when a selected layer, for example the erythrocyte layer, has reached a desired level in the blood bag.

In one aspect of the invention the device also has a second automatic shut-off function which stops the squeezing process when a predetermined residual volume remains in the blood bag. This can conveniently be achieved by means of adjustable spacing means provided at the pressure plate or the stationary plate, said means preventing further compression of the blood bag.

The squeezing procedure is considerably simplified by means of a squeezing device having the above described characteristics. When using a conventional blood bag, wherein blood plasma and the buffy coat layer are taken through openings in the upper portion of the bag, it is thus possible to stop the plasma flow automatically by the action of, for example, a photocell when the darker erythrocyte layer has reached a predetermined level, which is adjusted such that the buffy coat layer essentially has reached the top edge of the bag. The buffy coat layer is then squeezed out, possibly by manual assistance. If desired, the blood plasma bag can then be centrifugated for separating thrombocytes. The above mentioned second shut-off function is in this case adjusted such that the squeezing will be interrupted at a predetermined residual volume in the plasma bag, which volume then should correspond to the volume of the thrombocyte layer obtained by the centrifugation, plus a certain volume of blood plasma. The squeezing is then carried out as above and will thus be stopped automatically when essentially all blood plasma has left the bag. In the same manner the original collection bag containing the erythrocytes can be centrifugated one more time for separating remaining thrombocytes and leucocytes. The centrifugation is in this case carried out with the bag in an upside down position so that the erythrocyte layer will be located closest to the outlet opening. The blood bag is then placed in the squeezing device in an upside down position so that erythrocytes will be squeezed out through the bottom of the bag. As indicated above the squeezing process will be interrupted automatically when essentially only thrombocytes and leucocytes remain in the blood bag.

The squeezing device according to the invention thus results in a considerably simplified procedure in conventional blood separation. The novel device is, however, especially suitable for use in a novel blood bag system for separation which is described in more detail in U.S. patent application Ser. No. 133,868, filed Mar. 25, 1980. The novel blood bag system is based on a blood bag having outlets at the top as well as at the bottom. During the squeezing operation the blood plasma will in this case be pressed out through the upper outlet while at the same time erythrocytes will be pressed out through the lower outlet. Because of the greater viscosity of the erythrocytes the plasma layer will, however, leave the blood bag more rapidly. The level of the layer containing erythrocytes will therefore move upwardly in the bag, and the plasma flow will be shut-off automatically as above by means of e.g. a photocell when it has reached the desired level in the blood bag. The bag will then be emptied only through the lower outlet, and as above the squeezing process will be interrupted automatically when a predetermined residual volume—essentially corresponding to the buffy coat layer—remains in the blood bag. In this manner an efficient separation of the blood components will be obtained rapidly and in simple manner.

In a variant the sensing means (one or more photocells or the like) are positioned essentially at the level of the buffy coat layer already from the start of the squeezing operation, and the sensing means are arranged to maintain the buffy coat layer at essentially the same level during the entire squeezing operation. In this embodiment the sensing means will alternatingly shut off and open the top outlet of the blood bag in response to the movements of the buffy coat layer. Thus, the sensing means will shut off the top outlet (leaving the bottom outlet open) when the buffy coat layer moves upwards. Correspondingly, the sensing means will open the top outlet when the buffy coat layer falls below the sensed level. An important advatage obtained when using this embodiment is that there will be only insignificant contact between the erythrocytes and the leucocytes sticking to the bag wall, resulting in a greater degree of purity of the separated red blood cell layer.

The squeezing device according to the invention can also advantageously be used in other separation techniques such as leucapheresis, plasmapheresis and thrombapheresis.

The invention will now be described in more detail with regard to a special embodiment to which it, however, is not restricted. Reference is made to the enclosed drawings, wherein FIG. 1 is a front perspective view of a squeezing device according to the invention, and FIG. 2 is a side perpective view of the device of FIG. 1 with certain portions broken away.

The device shown in the Figures comprises a stationary plate 1 forming the front wall of a box-like housing 2. A transparent pressure plate 3, for example made of plexiglass, is arranged essentially parallel to the wall 1 and attached to one end of two rods or bars 4 and 5 arranged perpendicularly to the front wall 1. The rods 4 and 5 are slidingly journalled in bores provided in the wall 1, for example by means of slide sleeves 6, made of teflon or the like and fitted into the bores. The opposite ends of the rods 4, 5 are attached to a plate 7. The rods 4 and 5 are also slidingly journalled in bores provided in an attachment plate 8 for a piston/cylinder assembly 9 positioned between the plate 8 and the wall 1, said plate being spaced apart from the wall 1. Also here slide sleeves 10 are conveniently provided in the bores. The attachment plate 8 keeps the piston/cylinder assembly 9 fixed against the wall 1 by means of two bolt joints 11. The piston/cylinder assembly 9 is arranged with the cylinder part between the plate 8 and the wall 1, and with the piston rod 12 slidingly journalled in a bore in the plate 8. The piston rod is at its free end attached to the plate 7 so that the motion of the piston/cylinder assembly results in a corresponding displacement of the pressure plate 3 in relation to the wall 1.

The piston/cylinder assembly can be hydraulic, pneumatic or hydropneumatic. In the illustrated case it consists of a compressed-air cylinder having compressed-air supply tubes 13a and 13b. These can be connected to a source of compressed-air by means of a valve device (not shown). The working pressure can be adjusted by means of a set screw 14 provided on the front plate 1 and connected to the valve device, and it can be read on a manometer 15. The air pressure is applied by means of a control 16 connected to the valve device.

Two photocells 17 and 18 are provided at the upper portion of the pressure plate 3, in the illustrated case on a column 19 attached to the pressure plate 3. The photocells 17, 18 are via a suitable circuit connected to a tube shut-off device 20 located on top of the housing 2. In the illustrated case the shut-off device 20 consists of a stationary stop means 21 and a pinch plate 22 which is journalled in the housing and displaceable towards said stop, the pinch plate being controlled by the photocells 17, 18 by means of any suitable control means. The latter can, for example, consist of an electromagnet or a compressed-air cylinder. The photocells 17, 18 are arranged to respond to the insertion of a darker surface between the photocells and the wall portion 1 so as to activate the control means and press the pinch plate 22 against the stop 21. The photocells 17, 18 are in the illustrated case activated and deactivated by means of a switch 23 and a convertor 24 for selecting the desired photocell. Light diodes 25a,25b indicate which photocell is activated. A main switch 26 is also provided on the front panel 1.

The pressure plate 3 is provided with a set screw 27. By means thereof spacing means provided at the inside of the pressure plate 3 can be adjusted such that the spacing means will stop the movement of the pressure plate 3 towards the wall 1 at the desired distance from the wall by contact between the spacing means and the wall 1. If desired, indicator means 28 can be provided on the pressure plate for indicating the adjustment expressed in any suitable unity.

In order to illustrate the function of the device there is shown in FIG. 1 a conventional blood bag 29 positioned between the pressure plate 3 and the wall 1. A tube conduit 30 leads from a top opening of the blood bag to a transfer bag (not shown). The tube 30 is arranged between the pinch plate 22 and the stop 21 of the shut-off means 20. The device operates in the following manner. After activating the device by means of the switch 26 and setting the desired working pressure by means of the set screw 14 the centrifugated blood bag, which contains an upper blood plasma layer, an intermediate buffy coat layer (leucocytes and possibly thrombocytes), and a lower layer of erythrocytes, is positioned between the pressure plate 3 and the wall 1. In this conventional type of blood bag the upper photocell 17 is used—for reasons to be indicated below—and it is activated by means of the switch 23 and the converter 24. A suspension device for the blood bag 29 can optionally be provided on the wall portion 1, but the most convenient is to pinch the blood bag in the desired position by means of the pressure plate 3. The driving of the pressure plate is controlled by means of the switch 16 for the piston/cylinder assembly 9. The blood bag 29 is positioned such that the photocell 17 will be located slightly below the outlet level of the blood bag. The piston/cylinder assembly 9 is then activated by means of the switch 16 to expell the piston rod 12 from the cylinder, thereby forcing the pressure plate 3 against the blood bag 29 via the plate 7 and the rods 4 and 5. The blood bag is compressed at constant pressure, the plasma layer being pressed out through the tube 30. When the layer containing erythrocytes and the thin buffy coat layer have reached the level of the photocell 17 the same will respond to the darker colour of these layers and activate the control means for the pinch plate 22 to press the same against the stop 21. In this manner the tube connection to the transfer bag will be shut-off and the plasma flow will be stopped. Since the drive means for the pressure plate 3 operate at constant pressure there is no risk that any harmful overpressure will be created in the blood bag 29. The major part of the plasma layer is now in the transfer bag, not shown. The connection to the same is shut-off, whereupon the power supply to the photocells is switched-off by means of the switch 23, and a further tube connection, not shown, to the top portion of the blood bag 29 is opened. The buffy coat layer will then start being squeezed out through said tube. Since the leucocytes have a tendency to stick to the wall of the bag it is mostly necessary to assist manually. For this reason the upper photocell 17 is positioned above the top edge of the pressure plate 3 to leave sufficient space for the fingers. The outlet tube in question can be a tube connection to a further transfer bag, but for cost reasons the buffy coat layer is often discharged through the tapping tube used when collecting the blood in the blood bag. When the buffy coat layer has been squeezed out the pressure plate is returned by means of the switch 16, and the blood bag 29 is removed after sealing of the respective tube connections. The separated components can then be used, worked up or stored as desired.

In case it is desired to centrifugate e.g. the transfer bag containing the transferred blood plasma layer for separating thrombocytes, the centrifugated bag is positioned between the pressure plate 3 and the wall portion 1 as before. In this case, however, the photocells 17, 18 are not used, but the set screw 27 is adjusted such that the final distance between the pressure plate 3 and the wall 1, which is determined by the spacing means associated with the set screw 27, corresponds to a predetermined residual volume in the transfer bag, namely the volume of the thrombocyte layer plus a certain volume of blood plasma. After activation the piston/cylinder assembly 9 the supernatant blood plasma layer is squeezed out, and the pressure plate 3 will stop at the desired distance from the wall 1 when the spacing means contact the same.

In the same manner the layer containing erythrocytes remaining in the original collection bag can be centrifugated further. It this case the centrifugation is carried out with the bag in an upside down position so that the layer containing erythrocytes will be located closest to the outlet opening. The bag is then inserted between the pressure plate 3 and the wall 1 with the outlet opening facing downwards, whereupon a squeezing operation is effected as above after adjustment of the set screw 27. When the spacing means of the set screw contact the wall 1, stopping the movement of the pressure plate, then consequently the layer containing erythrocytes has been squeezed out through the lower outlet, whereas thrombocytes, leucocytes and a safety volume of erythrocytes remain in the blood bag. When squeezing out the comparatively viscous layer of erythrocytes it may be necessary to increase the working pressure, using the set screw 14, for increasing the discharge rate.

As indicated above the novel device is especially suited for use in association with the above mentioned novel blood bag system, which is based on a blood collection bag having outlets at the top as well as at the bottom. Such a system for the separation of whole blood into blood plasma, a buffy coat layer, and erythrocytes comprises a collection bag having top and bottom outlets connected to a transfer bag. After conventional centrifugation of the blood bag system the collection bag is squeezed between the pressure plate 3 and the wall 1. The transfer bag connected to the top outlet can e.g. be positioned on top of the housing 1 with the tube running between the pinch plate 22 and the stop 21, and the transfer bag connected to the bottom outlet can, for example, be suspended on the column 19. In this type of blood bag the lower photocell 18 is used, the same being activated by means of the switch 23 and the converter 24. In place of two photocells 17, 18 it is also possible to use one single, movable photocell. The blood bag is adjusted in relation to the photocell 18 in the same manner as earlier described, and the set screw 27 is adjusted such that the final distance between the pressure plate 3 and the wall 1 will allow a residual volume in the blood bag substantially corresponding to the buffy coat layer and a small amount of erythrocytes. When displacing the pressure plate 3 towards the wall 1 blood plasma and erythrocytes will be pressed out simultaneously to the two transfer bags through the top and bottom outlets respectively of the blood bag. Because of the difference in viscosity between the layers the blood plasma will leave the blood bag more rapidly than the erythrocytes, and the level of the erythrocytes will therefore move upwards in the bag to finally reach the photocell 18. As earlier described the plasma flow will be shut-off automatically by means of the shut-off device 20. The squeezing out of erythrocytes will then continue until the spacing means associated with the set screw 27 reaches the wall 1. Only the buffy coat layer plus a small amount of erythrocytes then remain in the collection bag. By suspending, as mentioned above, the transfer bag intended for the erythrocytes on the column 19 the levels of the liquids in the same and in the collection bag will be at essentially the same level, thereby preventing the buffy coat layer from flowing to the transfer bag. In the above described manner, using the squeezing device according to the invention, there is obtained a simple and efficient blood component separation not requiring any surveillance.

In an alternative embodiment of the above described automated procedure, using a blood bag having both top and bottom outlets, the photocell 18 is positioned in the vicinity of the initial level of the buffy coat layer. As in the above procedure the photocell will shut off the connection between the blood bag and the transfer bag connected to its top portion when the buffy coat layer (or the top level of the erythrocyte layer) moves upwards and enters the level sensed by the photocell 18. Conversely, this connection will be reopened when the buffy coat layer falls below the sensed level. As a result the buffy coat layer will move up and down past the photocell 18 with a comparatively small amplitude of the movement. Thus, there will be a continuous flow of erythrocytes from the bottom outlet of the blood bag, and an intermittent flow of plasma through the top outlet of the blood bag, the level of the buffy coat layer being essentially constant all the time. As a result only the uppermost portion of the erythrocyte layer will get in contact with the leucocytes adhering to the wall of the bag. This in turn results in an improved separation of erythrocytes and leucocytes.

A suitable control circuit may optionally be provided for automatically increasing the pressure exerted by the pressure plate on the blood bag at the end of the squeezing process.

The drive means for the pressure plate 3 is not critical as such. In place of the described piston/cylinder assembly 9 one can thus also use any suitable electrical drive motor which, for example, is arranged to drive a threaded bar, a ball bearing screw or the like for displacement of the pressure plate 3. In such a case, however, any suitable means ought to be provided for preventing the pressure of the blood bag to exceed a predetermined level when the shut-off device 20 has stopped the plasma flow. The photocells 17, 18 may in this case optionally also be connected to the drive motor for stopping the same simultaneously with the activation of the shut-off device 20. A spring being tensioned manually by means of any suitable device can also be used as the drive means. The disadvantage is, however, that the pressure on the blood bag decreases with increasing compression of thereof. However, this disadvantage can be eliminated by using so-called gas springs. Since many laboratories are provided with compressed-air connections, compressed-air drive, as in the device illustrated in the Figure, ought to be suitable.

Although optical devices such as photocells are suitable for sensing the desired blood layer levels it is, of course, also possible to use other types of sensing means, for example such means based on ultra sonics.

The invention is, of course, not limited to the above specifically described embodiment, but many variations and modifications thereof are possible within the scope of the subsequent claims.

What we claim is:

1. Apparatus for the separation of whole blood components stratified within a blood bag by essentially uniform compression of said blood bag over the entire bag surface, said apparatus comprising (i) a stationary, rigid planar support surface; (ii) a rigid planar pressure surface fixedly disposed substantially parallel to said support surface (i) and perpendicularly displaceable relative thereto while maintaining said substantially parallel relationship; (iii) means for engagedly positioning and securing a flexible bag of stratified whole blood components comprising at least one outlet conduit between said support surface (i) and said pressure surface (ii); (iv) means for parallely biasing and displacing said pressure surface (ii) towards said support surface (i) along said perpendicular path of displacement and to exert an essentially uniform compressive force upon any blood bag engagedly positioned and secured therebetween, over essentially the entire surface thereof, to squeeze blood component from said at least one outlet conduit; (v) sensing means for automatically detecting when a pre-selected blood component layer has reached a given level in the blood bag; and (vi) means responsive to said sensing means (v) for automatically terminating the outlet flow of said pre-selected blood component from said blood bag.

2. The apparatus of claim 1 wherein said displacement means maintains an essentially constant pressure on a blood bag being compressed.

3. The apparatus of claim 1 wherein said displacement means causes the pressure on a blood bag being compressed to be increased during a compression operation.

4. The apparatus of claim 1 further including means for interrupting the displacement of said pressure surface towards said support surface when said surfaces are a given distance apart corresponding to a predetermined residual volume in a blood bag being compressed.

5. The apparatus of claim 4 wherein said interrupting means is adjustable to vary said given distance.

6. The apparatus of claim 4 or claim 5 wherein said interrupting means comprises a stop protruding from one of said pressure surface and said support surface.

7. The apparatus of claim 1 wherein said detecting means is mounted on said pressure surface.

8. The apparatus of claim 1 or claim 7 wherein said pressure surface is at least partially transparent.

9. The apparatus of claim 7 wherein said detecting means includes at least one sensing device mounted on the top edge of said pressure surface.

10. The apparatus of claim 1 further including a box-like stand, said support surface comprising a side wall thereof, said displacement means being disposed within said stand and being connected to said pressure surface by at least one elongate connection member extending through an opening in said side wall.

11. The apparatus of claim 1 wherein said detecting means is positioned at the initial level of a blood component layer in a blood bag to be compressed, and wherein said inhibiting means is responsive to said detecting means to allow fluid to flow through the outlet conduit when the blood component layer falls below said initial level and to inhibit the flow of fluid when the blood component layer reaches said initial level, to thereby maintain the blood component layer substantially at the initial level while the blood bag is being compressed.

12. The apparatus of claim 1 wherein said detecting means detects a color change between successive blood component layers.

13. The apparatus of claim 1 further comprising a flexible bag of stratified whole blood components, and comprising at least one outlet conduit, engagedly positioned and secured between said support surface and said pressure surface.

* * * * *